(12) United States Patent
Dietz et al.

(10) Patent No.: US 9,173,402 B2
(45) Date of Patent: Nov. 3, 2015

(54) FUNGICIDAL ALKYL-SUBSTITUTED 2[2-CHLORO-4-(4-CHIORO-PHENOXY)-PHENYL]-1[1,2,4]TRIAZOL-1-YL-ETHANOL COMPOUNDS

(75) Inventors: Jochen Dietz, Karlsruhe (DE); Richard Riggs, Mannheim (DE); Nadege Boudet, Hemsbach (DE); Jan Klaas Lohmann, Lambsheim (DE); Ian Robert Craig, Ludwigshafen (DE); Egon Haden, Speyer (DE); Erica May Wilson Lauterwasser, Mannheim (DE); Bernd Müller, Frankenthal (DE); Wassilios Grammenos, Ludwigshafen (DE); Thomas Grote, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/232,462

(22) PCT Filed: Jul. 11, 2012

(86) PCT No.: PCT/EP2012/063526
§ 371 (c)(1),
(2), (4) Date: Jan. 13, 2014

(87) PCT Pub. No.: WO2013/010862
PCT Pub. Date: Jan. 24, 2013

(65) Prior Publication Data
US 2014/0128255 A1 May 8, 2014

Related U.S. Application Data

(60) Provisional application No. 61/508,084, filed on Jul. 15, 2011.

(30) Foreign Application Priority Data

Jul. 15, 2011 (EP) ..................................... 11174174

(51) Int. Cl.
| | |
|---|---|
| C07D 249/08 | (2006.01) |
| A01N 43/653 | (2006.01) |
| A01N 43/02 | (2006.01) |
| C07D 405/06 | (2006.01) |
| C07D 303/18 | (2006.01) |
| C07D 303/48 | (2006.01) |

(52) U.S. Cl.
CPC .............. *A01N 43/653* (2013.01); *A01N 43/02* (2013.01); *C07D 249/08* (2013.01); *C07D 303/18* (2013.01); *C07D 303/48* (2013.01); *C07D 405/06* (2013.01)

(58) Field of Classification Search
CPC .................................................... C07D 249/08
USPC ....................................... 504/272; 548/267.8
See application file for complete search history.

(56) References Cited

U.S. PATENT DOCUMENTS

| | | | |
|---|---|---|---|
| 4,242,121 | A | 12/1980 | Hawkins et al. |
| 4,599,362 | A | 7/1986 | Nakatani et al. |
| 4,940,720 | A | 7/1990 | Nevill et al. |
| 4,945,100 | A | 7/1990 | Nyfeler et al. |
| 4,992,458 | A | 2/1991 | Riebli et al. |
| 5,143,932 | A | 9/1992 | Jautelat et al. |
| 5,162,358 | A | 11/1992 | Jautelat et al. |
| 2008/0108686 | A1 | 5/2008 | Gewehr et al. |
| 2009/0036509 | A1 | 2/2009 | Gewehr et al. |
| 2009/0286768 | A1 | 11/2009 | Crew et al. |

FOREIGN PATENT DOCUMENTS

| | | |
|---|---|---|
| AU | 611315 | 6/1991 |
| CA | 1100976 | 5/1981 |
| CA | 1209152 | 8/1986 |
| CN | 101225074 | 7/2008 |
| CS | 247 200 | 12/1986 |
| DE | 2 325 878 | 12/1974 |
| DE | 3801233 | 8/1988 |
| DE | 4003180 | 8/1991 |
| EP | 0 000 017 | 12/1978 |
| EP | 0113640 | 7/1984 |
| EP | 0126430 | 11/1984 |
| EP | 0275955 | 7/1988 |
| EP | 0 354 183 | 2/1990 |
| EP | 0 440 950 | 8/1991 |

(Continued)

OTHER PUBLICATIONS

Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.
International Preliminary Report on Patentability, issued in PCT/EP2012/063526, dated Oct. 1, 2013.
International Search Report, issued in PCT/EP2012/063526, dated Sep. 17, 2012.
Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.
Office Action dated Dec. 10, 2014, issued in U.S. Appl. No. 14/237,463.
Office Action dated Dec. 1, 2014, issued in U.S. Appl. No. 14/232,434.

(Continued)

*Primary Examiner* — Rebecca Anderson
*Assistant Examiner* — Karen Cheng
(74) *Attorney, Agent, or Firm* — Brinks Gilson & Lione

(57) ABSTRACT

The present invention relates to the use of alkyl-substituted 2-[2-chloro-4-(4-chloro-phenoxy)-phenyl]-1-[1,2,4]triazol-1-yl-ethanol compounds of formula I as defined in the description, and the N-oxides, and salts thereof for combating harmful fungi and seed coated with at least one such compound. The invention also relates to novel alkyl-substituted 2-[2-chloro-4-(4-chloro-phenoxy)-phenyl]-1-[1,2,4]triazol-1-yl-ethanol compounds, processes and intermediates for preparing these compounds and also to compositions comprising at least one such compound.

18 Claims, No Drawings

(56) References Cited

FOREIGN PATENT DOCUMENTS

| | | |
|---|---|---|
| EP | 0470466 | 2/1992 |
| EP | 1 431 275 | 6/2004 |
| FR | 2 491 924 | 4/1982 |
| GB | 2 132 195 | 7/1984 |
| WO | WO 96/41804 | 12/1996 |
| WO | WO 03 064572 | 8/2003 |
| WO | WO 2005/123689 | 12/2005 |
| WO | WO 2005/123690 | 12/2005 |
| WO | WO 2006/015866 | 2/2006 |
| WO | WO 2006/087373 | 8/2006 |
| WO | WO 2006/109933 | 10/2006 |
| WO | WO 2006/119876 | 11/2006 |
| WO | WO 2008/082198 | 7/2008 |
| WO | WO 2010/146114 | 12/2010 |
| WO | WO 2011/099804 | 8/2011 |
| WO | WO 2012/037782 | 3/2012 |
| WO | WO 2013/010885 | 1/2013 |
| WO | WO 2013/010894 | 1/2013 |
| WO | WO 2013/024076 | 1/2013 |
| WO | WO 2013/024077 | 1/2013 |
| WO | WO 2013/024082 | 1/2013 |
| WO | WO 2013007767 | 1/2013 |
| WO | WO 2013/024075 | 2/2013 |
| WO | WO 2013/024080 | 2/2013 |
| WO | WO 2013/024081 | 2/2013 |
| WO | WO 2013/024083 | 2/2013 |

OTHER PUBLICATIONS

Office Action dated Dec. 8, 2014, issued in U.S. Appl. No. 14/237,048.

Lima, Lidia Moreira et al., "Bioisosterism: A useful strategy for molecular Modification and drug design", Current Medicinal Chemistry, 2005, p. 23-49, vol. 12.

FUNGICIDAL ALKYL-SUBSTITUTED 2[2-CHLORO-4-(4-CHlORO-PHENOXY)-PHENYL]-1[1,2,4]TRIAZOL-1-YL-ETHANOL COMPOUNDS

This application is a National Stage application of International Application No. PCT/EP2012/063526, filed Jul. 11, 2012, which claims the benefit of U.S. Provisional Application No. 61/508,084, filed Jul. 15, 2011. This application also claims priority under 35 U.S.C. §119 to European Patent Application No. 11174174.1, filed Jul. 15, 2011.

The present invention relates to the use of alkyl-substituted 2-[2-chloro-4-(4-chloro-phenoxy)-phenyl]-1-[1,2,4]triazol-1-yl-ethanol compounds and the N-oxides and the salts thereof for combating phytopathogenic fungi, and to methods for combating phytopathogenic fungi and to seeds coated with at least one such compound. The invention also relates to novel 2-[2-chloro-4-(4-chloro-phenoxy)-phenyl]-1-[1,2,4]triazol-1-yl-propan-2-ol derivatives, processes for preparing these compounds and to compositions comprising at least one such compound.

The use of 2-[2-chloro-4-(4-chloro-phenoxy)-phenyl]-1-[1,2,4]triazol-1-yl-ethanol and certain derivatives thereof of formula

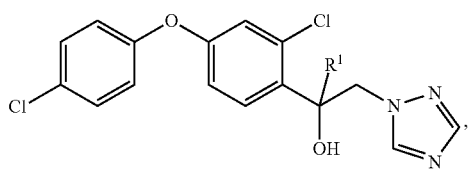

wherein $R^1$ is inter alia methyl or a hydroxy-, methoxy- or amine-substituted derivative of methyl or an aryl-substituted alkenyl, for controlling phytopathogenic fungi is known from EP 0 275 955 A1 and J. Agric. Food Chem. (2009) 57, 4854-4860.

Further, the fungicidal use of compounds of the abovementioned formula wherein $R^1$ is halogenalkyl, e.g. fluoromethyl or 2,2,3,3-tetrachloropropyl, has been mentioned in EP 0 113 640 A2 and EP 0 470 466 A2.

In addition, the fungicidal use of compounds of the abovementioned formula in which $R^1$ is halogenallyl, specifically 2,3-dibromo-allyl, have been mentioned in DE 40 03 180 A1.

The compounds according to the present invention differ from those described in the abovemention publications inter alia by the replacement of the above-mentioned methyl, halogenalkyl or halogenallyl groups by the specific substituent $R^1$ as defined herein.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by the use of certain alkyl-substituted 2-[2-chloro-4-(4-chloro-phenoxy)-phenyl]-1-[1,2,4]triazol-1-yl-ethanol derivatives having good fungicidal activity against phytopathogenic harmful fungi.

Accordingly, the present invention relates to the use of compounds of formula I:

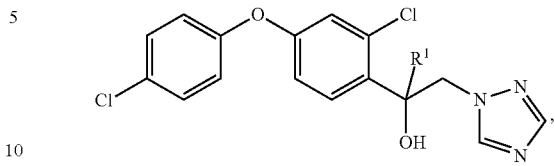

wherein:
$R^1$ is $C_2$-$C_6$-alkyl, $C_2$-$C_6$-alkenyl, $C_2$-$C_6$-alkynyl, $C_3$-$C_8$-cycloalkyl or $C_3$-$C_8$-cycloalkyl-$C_1$-$C_4$-alkyl;
  wherein the aliphatic groups $R^1$ are unsubstituted or carry 1, 2, 3 or 4 CN substituents;
  wherein the cycloalkyl moieties of $R^1$ are unsubstituted or carry 1, 2, 3 or up to the maximum number of identical or different groups $R^b$ which independently of one another are selected from:
    $R^b$ halogen, CN, nitro, $C_1$-$C_4$-alkyl, $C_1$-$C_4$-alkoxy, $C_1$-$C_4$-halogenalkyl and $C_1$-$C_4$-halogenalkoxy;
and the N-oxides and the agriculturally acceptable salts thereof;
for combating phytopathogenic harmful fungi.

The preparation of 2-[2-chloro-4-(4-chloro-phenoxy)-phenyl]-1-[1,2,4]triazol-1-yl-pent-4-yn-2-ol is disclosed in DE 40 03 180 A1.

The compounds according to the present invention differ from those described in the abovementioned publication by the specific definition of $R^1$ and by the proviso that formula I cannot be 2-[2-chloro-4-(4-chloro-phenoxy)-phenyl]-1-[1,2,4]triazol-1-yl-pent-4-yn-2-ol.

Therefore, according to a second aspect, the invention provides compounds of formula I which are represented by formula I having good fungicidal activity against phytopathogenic harmful fungi:

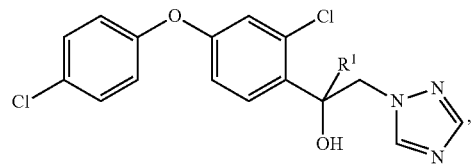

wherein:
$R^1$ is $C_2$-$C_6$-alkyl, $C_2$-$C_6$-alkenyl or $C_2$-$C_6$-alkynyl, $C_3$-$C_8$-cycloalkyl, $C_3$-$C_8$-cycloalkyl-$C_1$-$C_4$-alkyl;
  wherein the aliphatic groups $R^1$ are unsubstituted or carry 1, 2, 3 or 4 CN substituents;
  wherein the cycloalkyl moieties of $R^1$ are unsubstituted or carry 1, 2, 3, or up to the maximum number of identical or different groups $R^b$ which independently of one another are selected from:
    $R^b$ halogen, CN, nitro, $C_1$-$C_4$-alkyl, $C_1$-$C_4$-alkoxy, $C_1$-$C_4$-halogenalkyl and $C_1$-$C_4$-halogenalkoxy;
and the N-oxides and the agriculturally acceptable salts thereof,
except for 2-[2-chloro-4-(4-chloro-phenoxy)-phenyl]-1-[1,2,4]triazol-1-yl-pent-4-yn-2-ol.

The term "compounds I" refers to compounds of formula I. Likewise, this terminology applies to all sub-formulae, e.g. "compounds I.A" refers to compounds of formula I.A or "compounds XI" refers to compounds of formula XI, etc.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2) and by the synthesis routes shown in the following schemes and in the experimental part of this application.

In a first process, for example, 4-chlorophenole II is reacted, in a first step, with bromo derivatives III wherein Y is F or Cl, preferably in the presence of a base. Thereafter, the resulting compounds IV are then transformed into Grignard reagents by the reaction with transmetallation reagents such as isopropylmagnesium halides and subsequently reacted with acetyl chloride preferably under anhydrous conditions and optionally in the presence of a catalyst such as CuCl, AlCl$_3$, LiCl and mixtures thereof, to obtain acetophenones V.

These compounds V can be halogenated e.g. with bromine preferably in an organic solvent such as diethyl ether, methyl tert.-butyl ether (MTBE), methanol or acetic acid. The resulting compounds VI can subsequently reacted with 1H-1,2,4-triazole preferably in the presence of a solvent such as tetrahydrofuran (THF), dimethylormamide (DMF), toluene and in the presence of a base such as potassium carbonate, sodium hydroxide or sodium hydride to obtain compounds VII. These triazole compounds VII are reacted with a Grignard reagent R$^1$-M of formula VIII wherein R$^1$ is as defined above and M is MgBr, MgCl, Li or Na (e.g. phenylalkyl-MgBr or an organolithium reagent phenylalkyl-Li), preferably under anhydrous conditions to obtain compounds I, optionally using a Lewis acid such as LaCl$_3$×2LiCl or MgBr$_2$×OEt$_2$. The preparation of compounds I can be illustrated by the following scheme:

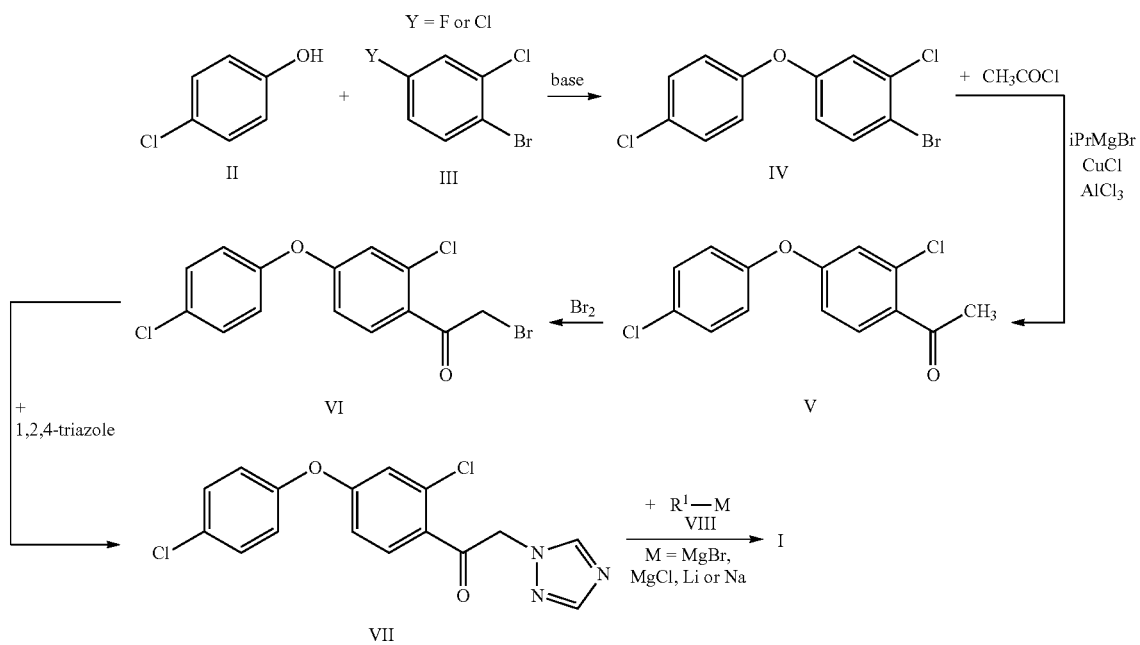

In a second process to obtain compounds I, bromo derivatives III, in a first step, are reacted with e.g. isopropylmagnesium bromide followed by an acyl chloride agent IX wherein R$^1$ is as defined above (e.g. acetyl chloride) preferably under anhydrous conditions and optionally in the presence of a catalyst such as CuCl, AlCl$_3$, LiCl and mixtures thereof, to obtain compounds X. Alternatively, 1,3-dichlorobenzene of formula IIIb can be reacted with an acyl chloride agent IX wherein R$^1$ is as defined above (e.g. acetyl chloride) preferably in the presence of a catalyst such as AlCl$_3$. Then, ketones X are reacted with phenoles II preferably in the presence of a base to obtain compounds Va.

Thereafter, intermediates Va are reacted with trimethylsulf(ox)onium halides preferably iodide preferably in the presence of a base such as sodium hydroxide. Thereafter, the epoxides XI are reacted with 1H-1,2,4-triazole preferably in the presence of a base such as potassium carbonate and preferably in the presence of an organic solvent such as DMF to obtain compounds I. The preparation of compounds I can be illustrated by the following scheme:

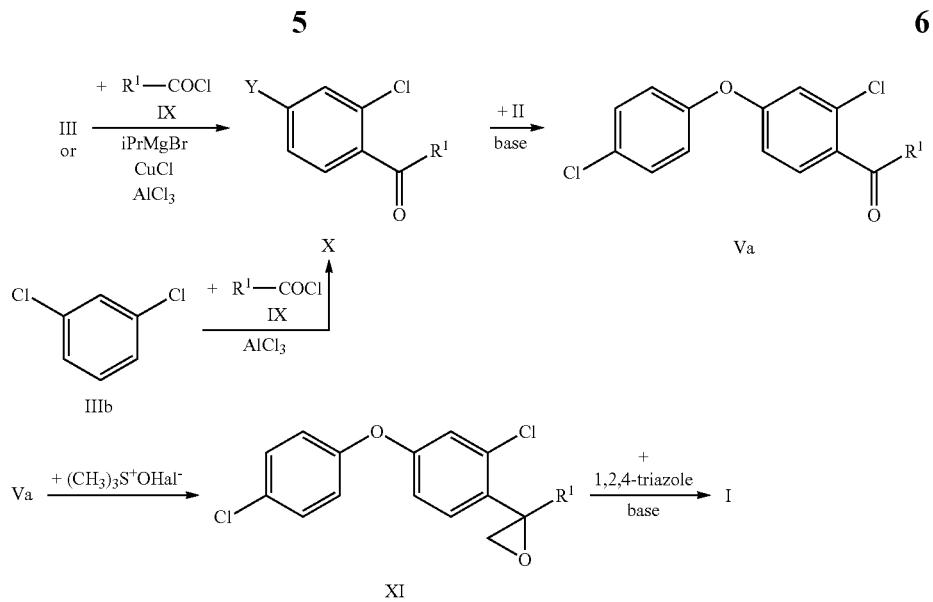

The compound Va can be generically prepared using intermediate IV with a grignard reagent such as iPrMgBr and the corresponding acyl chloride $R_1COCl$, optionally in presence of catalyst such as CuCl, $AlCl_3$, LiCl.

If individual compounds I cannot be obtained by the routes described above, they can be prepared by derivatization of other compounds I.

The N-oxides may be prepared from the compounds I according to conventional oxidation methods, e.g. by treating compounds I with an organic peracid such as meta-chloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the harmful fungus to be controlled.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_2$-$C_6$-alkyl" refers to a straight-chained or branched saturated hydrocarbon group having 2 to 6 carbon atoms, e.g. ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms.

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, 1-propynyl, 1-butynyl, 2-butynyl, 3-butynyl, 1-methyl-2-propynyl. Likewise, the term "$C_2$-$C_6$-alkynyl" refers to a straight-chain or branched unsaturated hydrocarbon radical having 2 to 6 carbon atoms and at least one triple bond.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae and to the intermediates such as compounds XI, wherein the substituents (such as $R^1$) have independently of each other or more preferably in combination the following meanings:

One embodiment relates to compounds I, wherein $R^1$ is $C_2$-$C_4$-alkyl, $C_2$-$C_4$-alkenyl or $C_2$-$C_4$-alkynyl.

Another embodiment relates to compounds I, wherein $R^1$ is $C_2$-$C_6$-alkyl. Preferably $R^1$ is $C_2$-$C_4$-alkyl.

In a further embodiment of the invention $R^1$ is ethyl.
In a further embodiment of the invention $R^1$ is n-propyl.
In a further embodiment of the invention $R^1$ is iso-propyl.
In a further embodiment of the invention $R^1$ is n-butyl
In a further embodiment of the invention $R^1$ is tert.-butyl.

A further embodiment relates to compounds I, wherein $R^1$ is ethyl, n-propyl, isopropyl, n-butyl, tert.-butyl, allyl, ethynyl, prop-1-ynyl; but-1-ynyl, cyclopropyl or cyclopropylmethyl.

A further embodiment relates to compounds I, wherein $R^1$ is $C_2$-$C_6$-alkenyl. Preferably $R^1$ is $C_2$-$C_4$-alkenyl.

In a further embodiment of the invention $R^1$ is vinyl.
In a further embodiment of the invention $R^1$ is allyl.

A further embodiment relates to compounds I, wherein $R^1$ is $C_2$-$C_6$-alkynyl. Preferably $R^1$ is $C_2$-$C_6$-alk-1-ynyl.

In a further embodiment of the invention $R^1$ isethynyl.
In a further embodiment of the invention $R^1$ is prop-1-ynyl.
In a further embodiment of the invention $R^1$ isbut-1-ynyl.
In a further embodiment of the invention $R^1$ is 3-methylbut-1-ynyl.
In a further embodiment of the invention $R^1$ is 3,3-dimethylbut-1-ynyl.

A further embodiment relates to compounds I, wherein $R^1$ is $C_2$-$C_4$-alkynyl, preferably $C_2$-$C_4$-alk-1-ynyl, even more preferably selected from ethynyl and but-1-ynyl.

A further embodiment relates to compounds I, wherein $R^1$ is $C_3$-$C_8$-cycloalkyl.

In a further embodiment of the invention $R^1$ is cyclopropyl.
A further embodiment relates to compounds I, wherein $R^1$ is $C_3$-$C_8$-cycloalkyl-$C_1$-$C_4$-alkyl
In a further embodiment of the invention $R^1$ is cyclopropylmethyl.
A further embodiment relates to compounds I, wherein $R^1$ does not carry any CN substituent.
A further embodiment relates to compounds I, wherein $R^1$ does not carry any group $R^b$.

A further embodiment relates to compounds I, wherein the cycloalkyl moiety of $R^1$ carries 1 to 3 $R^b$ groups selected from halogen.

A skilled person will readily understand that the preferences given in connection with compounds I apply for formulae I and XI as defined above.

With respect to their use, particular preference is given to the 48 compounds of formulae I.A, and XI compiled in Table 1 below. Here, the groups mentioned in the Tables for a substituent are furthermore, independently of the combination wherein they are mentioned, a particularly preferred embodiment of the substituent in question.

Table 1: Compounds 1 to 48 of Formula I, Wherein the Meaning of $R^1$ for Each Individual Compound Corresponds in Each Case to One Line in Table A.

TABLE A

| No. | $R^1$ |
|---|---|
| 1 | —$CH_2CH_3$ |
| 2 | —$CH_2CH_2CH_3$ |
| 3 | —$CH(CH_3)_2$ |
| 4 | —$CH_2CH_2CH_2CH_3$ |
| 5 | —$CH(CH_2CH_3)_2$ |
| 6 | —$C(CH_3)_3$ |
| 7 | —$CH_2CH(CH_3)_2$ |
| 8 | —$CH_2CH_2CH_2CH_2CH_3$ |
| 9 | —$CH_2CH_2CH_2CH_2CH_2CH_3$ |
| 10 | —CH=$CH_2$ |
| 11 | —CH=$CHCH_3$ |
| 12 | —$CH_2$CH=$CH_2$ |
| 13 | —C($CH_3$)=$CH_2$ |
| 14 | —CH=$CHCH_2CH_3$ |
| 15 | —$CH_2$CH=$CHCH_3$ |
| 16 | —$CH_2CH_2$CH=$CH_2$ |
| 17 | —CH(CH=$CH_2)_2$ |
| 18 | —CH=C($CH_3)_2$ |
| 19 | —CH=$CHCH_2CH_2CH_3$ |
| 20 | —CH=$CHCH_2CH_2CH_2CH_3$ |
| 21 | —CH=$CHC(CH_3)_3$ |
| 22 | —C≡CH |
| 23 | —C≡$CCH_3$ |
| 24 | —C≡$CCH_2CH_3$ |
| 25 | —$CH_2$C≡$CCH_3$ |
| 26 | —$CH_2CH_2$C≡CH |
| 27 | —CH(C≡CH)$_2$ |
| 28 | —C≡$CCH_2CH_2CH_3$ |
| 29 | —C≡$CCH(CH_3)_2$ |
| 30 | —C≡$CCH_2CH_2CH_2CH_3$ |
| 31 | —C≡$CC(CH_3)_3$ |
| 32 | —$C_3H_5$ (cyclopropyl) |
| 33 | 1-Cl-cyclopropyl |
| 34 | 1-F-cyclopropyl |
| 35 | —$C_4H_7$ |
| 36 | —$C_6H_{11}$ (cyclohexyl) |
| 37 | —$CH_2$—$C_3H_5$ |
| 38 | —$CH_2$—CN |
| 39 | —$CH_2CH_2$—CN |
| 40 | —$CH_2$—C($CH_3$)=$CH_2$ |
| 41 | —$C_5H_9$ (cyclopentyl) |
| 42 | —CH($CH_3$)$CH_2CH_3$ |
| 43 | —$CH_2$C≡CH |
| 44 | —$CH_2$C≡$CCH_2CH_3$ |
| 45 | —CH($CH_3$)$C_3H_5$ |
| 46 | 1-Methyl-cyclopropyl |
| 47 | 1-CN-cyclopropyl |
| 48 | —CH($CH_3$)CN |

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. indemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri* Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoi*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broadleaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. scerotiorum*) and soybeans (e.g. *S. rolfsii* or *S. scerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setosphaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I and 5-15 wt % wetting agent (e.g. alcohol alkoxylates) are dissolved in water and/or in a water-soluble solvent (e.g. alcohols) up to 100 wt %. The active substance dissolves upon dilution with water.
ii) Dispersible Concentrates (DC)

5-25 wt % of a compound I and 1-10 wt % dispersant (e.g. polyvinylpyrrolidone) are dissolved in up to 100 wt % organic solvent (e.g. cyclohexanone). Dilution with water gives a dispersion.
iii) Emulsifiable Concentrates (EC)

15-70 wt % of a compound I and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.
iv) Emulsions (EW, EO, ES)

5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.
v) Suspensions (SC, OD, FS)

In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.
vi) Water-Dispersible Granules and Water-Soluble Granules (WG, SG)

50-80 wt % of a compound I are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.
vii) Water-Dispersible Powders and Water-Soluble Powders (WP, SP, WS)

50-80 wt % of a compound I are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.
viii) Gel (GW, GF)

In an agitated ball mill, 5-25 wt % of a compound I are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.
iv) Microemulsion (ME)

5-20 wt % of a compound I are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.
iv) Microcapsules (CS)

An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.
ix) Dustable Powders (DP, DS)

1-10 wt % of a compound I are ground finely and mixed intimately with up to 100 wt % solid carrier, e.g. finely divided kaolin.
x) Granules (GR, FG)

0.5-30 wt % of a compound I is ground finely and associated with up to 100 wt % solid carrier (e.g. silicate). Granulation is achieved by extrusion, spray-drying or the fluidized bed.
xi) Ultra-Low Volume Liquids (UL)

1-50 wt % of a compound I are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I can be used, is intended to illustrate the possible combinations but does not limit them:

A) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide; 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic Acid Synthesis Inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy) pyrimidin-4-amine;

D) Inhibitors of Cell Division and Cytoskeleton tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of Amino Acid and Protein Synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloridehydrate, mildiomycin, streptomycin, oxytetracyclin, polyoxine, validamycin A;

F) Signal Transduction Inhibitors

MAP/histidine kinase inhibitors: fluoroimid, iprodione, procymidone, vinclozolin, fenpiclonil, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

compounds affecting cell membrane permeability and fatty acides: propamocarb, propamocarb-hydrochlorid;

fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

guanidines and others: guanidine, dodine, dodine free base, guazatine, guazatineacetate, iminoctadine, iminoctadine-triacetate, iminoctadine-tris(albesilate), dithianon; 2,6-dimethyl-1H,5H-[1,4]dithiino[2,3-c:5,6-c']dipyrrole-1,3,5,7(2H,6H)tetraone;

I) Cell Wall Synthesis Inhibitors inhibitors of glucan synthesis: validamycin, polyoxin B;

melanin synthesis inhibitors: pyroquilon, tricyclazole, carpropamid, dicyclomet, fenoxanil;

J) Plant Defence Inducers acibenzolar-S-methyl, probenazole, isotianil, tiadinil, prohexadione-calcium; phosphonates: fosetyl, fosetyl-aluminum, phosphorous acid and its salts;

K) Unknown Mode of Action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl form amidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1 H-pyrazol-1-yl)-acetyl]-piperidin-4-yl}-N-[(1R)-1,2,3,4-tetrahydro-naphthalen-1-yl]-4-thiazolecarboxamide, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amylolique-faciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b] pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chlorophenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino- 3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e.g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines B-1 to B-360 of Table B.

A further embodiment relates to the compositions B-1 to B-360 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
|---|---|---|
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |
| B-30 | one individualized compound I | Fluxapyroxad |

TABLE B-continued

Composition comprising one indiviualized compound I
and one further active substance from groups A) to O)

| Mixture | Component 1 | Component 2 |
|---|---|---|
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |
| B-45 | one individualized compound I | Thifluzamide |
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | Dimethomorph |
| B-52 | one individualized compound I | Flumorph |
| B-53 | one individualized compound I | Pyrimorph |
| B-54 | one individualized compound I | Flumetover |
| B-55 | one individualized compound I | Fluopicolide |
| B-56 | one individualized compound I | Fluopyram |
| B-57 | one individualized compound I | Zoxamide |
| B-58 | one individualized compound I | Carpropamid |
| B-59 | one individualized compound I | Diclocymet |
| B-60 | one individualized compound I | Mandipropamid |
| B-61 | one individualized compound I | Oxytetracyclin |
| B-62 | one individualized compound I | Silthiofam |
| B-63 | one individualized compound I | N-(6-methoxy-pyridin-3-yl) cyclopropanecarboxylic acid amide |
| B-64 | one individualized compound I | Azaconazole |
| B-65 | one individualized compound I | Bitertanol |
| B-66 | one individualized compound I | Bromuconazole |
| B-67 | one individualized compound I | Cyproconazole |
| B-68 | one individualized compound I | Difenoconazole |
| B-69 | one individualized compound I | Diniconazole |
| B-70 | one individualized compound I | Diniconazole-M |
| B-71 | one individualized compound I | Epoxiconazole |
| B-72 | one individualized compound I | Fenbuconazole |
| B-73 | one individualized compound I | Fluquinconazole |
| B-74 | one individualized compound I | Flusilazole |
| B-75 | one individualized compound I | Flutriafol |
| B-76 | one individualized compound I | Hexaconazol |
| B-77 | one individualized compound I | Imibenconazole |
| B-78 | one individualized compound I | Ipconazole |
| B-79 | one individualized compound I | Metconazole |
| B-80 | one individualized compound I | Myclobutanil |
| B-81 | one individualized compound I | Oxpoconazol |
| B-82 | one individualized compound I | Paclobutrazol |
| B-83 | one individualized compound I | Penconazole |
| B-84 | one individualized compound I | Propiconazole |
| B-85 | one individualized compound I | Prothioconazole |
| B-86 | one individualized compound I | Simeconazole |
| B-87 | one individualized compound I | Tebuconazole |
| B-88 | one individualized compound I | Tetraconazole |
| B-89 | one individualized compound I | Triadimefon |
| B-90 | one individualized compound I | Triadimenol |
| B-91 | one individualized compound I | Triticonazole |
| B-92 | one individualized compound I | Uniconazole |
| B-93 | one individualized compound I | Cyazofamid |
| B-94 | one individualized compound I | Imazalil |
| B-95 | one individualized compound I | Imazalil-sulfate |
| B-96 | one individualized compound I | Pefurazoate |

TABLE B-continued

Composition comprising one indiviualized compound I
and one further active substance from groups A) to O)

| Mixture | Component 1 | Component 2 |
|---|---|---|
| B-97 | one individualized compound I | Prochloraz |
| B-98 | one individualized compound I | Triflumizole |
| B-99 | one individualized compound I | Benomyl |
| B-100 | one individualized compound I | Carbendazim |
| B-101 | one individualized compound I | Fuberidazole |
| B-102 | one individualized compound I | Thiabendazole |
| B-103 | one individualized compound I | Ethaboxam |
| B-104 | one individualized compound I | Etridiazole |
| B-105 | one individualized compound I | Hymexazole |
| B-106 | one individualized compound I | 2-(4-Chloro-phenyl)-N-[4-(3,4-dimethoxy-phenyl)-isoxazol-5-yl]-2-prop-2-yn-yloxy-acetamide |
| B-107 | one individualized compound I | Fluazinam |
| B-108 | one individualized compound I | Pyrifenox |
| B-109 | one individualized compound I | 3-[5-(4-Chloro-phenyl)-2,3-dimethyl-isoxazolidin-3-yl]-pyridine (Pyrisoxazole) |
| B-110 | one individualized compound I | 3-[5-(4-Methyl-phenyl)-2,3-dimethyl-isoxazolidin-3-yl]-pyridine |
| B-111 | one individualized compound I | Bupirimate |
| B-112 | one individualized compound I | Cyprodinil |
| B-113 | one individualized compound I | 5-Fluorocytosine |
| B-114 | one individualized compound I | 5-Fluoro-2-(p-tolylmethoxy)pyrimidin-4-amine |
| B-115 | one individualized compound I | 5-Fluoro-2-(4-fluorophenylmethoxy)-pyrimidin-4-amine |
| B-116 | one individualized compound I | Diflumetorim |
| B-117 | one individualized compound I | (5,8-Difluoroquinazolin-4-yl)-{2-[2-fluoro-4-(4-trifluoromethylpyridin-2-yloxy)-phenyl]-ethyl}-amine |
| B-118 | one individualized compound I | Fenarimol |
| B-119 | one individualized compound I | Ferimzone |
| B-120 | one individualized compound I | Mepanipyrim |
| B-121 | one individualized compound I | Nitrapyrin |
| B-122 | one individualized compound I | Nuarimol |
| B-123 | one individualized compound I | Pyrimethanil |
| B-124 | one individualized compound I | Triforine |
| B-125 | one individualized compound I | Fenpiclonil |
| B-126 | one individualized compound I | Fludioxonil |
| B-127 | one individualized compound I | Aldimorph |
| B-128 | one individualized compound I | Dodemorph |
| B-129 | one individualized compound I | Dodemorph-acetate |
| B-130 | one individualized compound I | Fenpropimorph |
| B-131 | one individualized compound I | Tridemorph |
| B-132 | one individualized compound I | Fenpropidin |
| B-133 | one individualized compound I | Fluoroimid |
| B-134 | one individualized compound I | Iprodione |
| B-135 | one individualized compound I | Procymidone |
| B-136 | one individualized compound I | Vinclozolin |
| B-137 | one individualized compound I | Famoxadone |
| B-138 | one individualized compound I | Fenamidone |
| B-139 | one individualized compound I | Flutianil |
| B-140 | one individualized compound I | Octhilinone |
| B-141 | one individualized compound I | Probenazole |
| B-142 | one individualized compound I | Fenpyrazamine |
| B-143 | one individualized compound I | Acibenzolar-S-methyl |
| B-144 | one individualized compound I | Ametoctradin |
| B-145 | one individualized compound I | Amisulbrom |
| B-146 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| B-147 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| B-148 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| B-149 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |

TABLE B-continued

Composition comprising one indiviualized compound I
and one further active substance from groups A) to O)

| Mixture | Component 1 | Component 2 |
|---|---|---|
| B-150 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methyl-propanoate |
| B-151 | one individualized compound I | Anilazin |
| B-152 | one individualized compound I | Blasticidin-S |
| B-153 | one individualized compound I | Captafol |
| B-154 | one individualized compound I | Captan |
| B-155 | one individualized compound I | Chinomethionat |
| B-156 | one individualized compound I | Dazomet |
| B-157 | one individualized compound I | Debacarb |
| B-158 | one individualized compound I | Diclomezine |
| B-159 | one individualized compound I | Difenzoquat, |
| B-160 | one individualized compound I | Difenzoquat-methylsulfate |
| B-161 | one individualized compound I | Fenoxanil |
| B-162 | one individualized compound I | Folpet |
| B-163 | one individualized compound I | Oxolinsäure |
| B-164 | one individualized compound I | Piperalin |
| B-165 | one individualized compound I | Proquinazid |
| B-166 | one individualized compound I | Pyroquilon |
| B-167 | one individualized compound I | Quinoxyfen |
| B-168 | one individualized compound I | Triazoxid |
| B-169 | one individualized compound I | Tricyclazole |
| B-170 | one individualized compound I | 2-Butoxy-6-iodo-3-propyl-chromen-4-one |
| B-171 | one individualized compound I | 5-Chloro-1-(4,6-dimethoxy-pyrimidin-2-yl)-2-methyl-1H-benzoimidazole |
| B-172 | one individualized compound I | 5-Chloro-7-(4-methyl-piperidin-1-yl)-6-(2,4,6-trifluoro-phenyl)-[1,2,4]triazolo[1,5-a]pyrimidine |
| B-173 | one individualized compound I | Ferbam |
| B-174 | one individualized compound I | Mancozeb |
| B-175 | one individualized compound I | Maneb |
| B-176 | one individualized compound I | Metam |
| B-177 | one individualized compound I | Methasulphocarb |
| B-178 | one individualized compound I | Metiram |
| B-179 | one individualized compound I | Propineb |
| B-180 | one individualized compound I | Thiram |
| B-181 | one individualized compound I | Zineb |
| B-182 | one individualized compound I | Ziram |
| B-183 | one individualized compound I | Diethofencarb |
| B-184 | one individualized compound I | Benthiavalicarb |
| B-185 | one individualized compound I | Iprovalicarb |
| B-186 | one individualized compound I | Propamocarb |
| B-187 | one individualized compound I | Propamocarb hydrochlorid |
| B-188 | one individualized compound I | Valifenalate |
| B-189 | one individualized compound I | N-(1-(1-(4-cyanophenyl)ethanesulfonyl)-but-2-yl) carbamic acid-(4-fluoro-phenyl) ester |
| B-190 | one individualized compound I | Dodine |
| B-191 | one individualized compound I | Dodine free base |
| B-192 | one individualized compound I | Guazatine |
| B-193 | one individualized compound I | Guazatine-acetate |
| B-194 | one individualized compound I | Iminoctadine |
| B-195 | one individualized compound I | Iminoctadine-triacetate |
| B-196 | one individualized compound I | Iminoctadine-tris(albesilate) |
| B-197 | one individualized compound I | Kasugamycin |
| B-198 | one individualized compound I | Kasugamycin-hydrochloride-hydrate |
| B-199 | one individualized compound I | Polyoxine |
| B-200 | one individualized compound I | Streptomycin |
| B-201 | one individualized compound I | Validamycin A |
| B-202 | one individualized compound I | Binapacryl |
| B-203 | one individualized compound I | Dicloran |
| B-204 | one individualized compound I | Dinobuton |
| B-205 | one individualized compound I | Dinocap |
| B-206 | one individualized compound I | Nitrothal-isopropyl |
| B-207 | one individualized compound I | Tecnazen |
| B-208 | one individualized compound I | Fentin salts |
| B-209 | one individualized compound I | Dithianon |
| B-210 | one individualized compound I | Isoprothiolane |
| B-211 | one individualized compound I | Edifenphos |
| B-212 | one individualized compound I | Fosetyl, Fosetyl-aluminium |
| B-213 | one individualized compound I | Iprobenfos |
| B-214 | one individualized compound I | Phosphorous acid ($H_3PO_3$) and derivatives |

TABLE B-continued

Composition comprising one indiviualized compound I
and one further active substance from groups A) to O)

| Mixture | Component 1 | Component 2 |
|---|---|---|
| B-215 | one individualized compound I | Pyrazophos |
| B-216 | one individualized compound I | Tolclofos-methyl |
| B-217 | one individualized compound I | Chlorothalonil |
| B-218 | one individualized compound I | Dichlofluanid |
| B-219 | one individualized compound I | Dichlorophen |
| B-220 | one individualized compound I | Flusulfamide |
| B-221 | one individualized compound I | Hexachlorbenzene |
| B-222 | one individualized compound I | Pencycuron |
| B-223 | one individualized compound I | Pentachlorophenol and salts |
| B-224 | one individualized compound I | Phthalide |
| B-225 | one individualized compound I | Quintozene |
| B-226 | one individualized compound I | Thiophanate Methyl |
| B-227 | one individualized compound I | Tolylfluanid |
| B-228 | one individualized compound I | N-(4-chloro-2-nitro-phenyl)-N-ethyl-4-methyl-benzenesulfonamide |
| B-229 | one individualized compound I | Bordeaux mixture |
| B-230 | one individualized compound I | Copper acetate |
| B-231 | one individualized compound I | Copper hydroxide |
| B-232 | one individualized compound I | Copper oxychloride |
| B-233 | one individualized compound I | basic Copper sulfate |
| B-234 | one individualized compound I | Sulfur |
| B-235 | one individualized compound I | Biphenyl |
| B-236 | one individualized compound I | Bronopol |
| B-237 | one individualized compound I | Cyflufenamid |
| B-238 | one individualized compound I | Cymoxanil |
| B-239 | one individualized compound I | Diphenylamin |
| B-240 | one individualized compound I | Metrafenone |
| B-241 | one individualized compound I | Pyriofenone |
| B-242 | one individualized compound I | Mildiomycin |
| B-243 | one individualized compound I | Oxin-copper |
| B-244 | one individualized compound I | Prohexadione calcium |
| B-245 | one individualized compound I | Spiroxamine |
| B-246 | one individualized compound I | Tebufloquin |
| B-247 | one individualized compound I | Tolylfluanid |
| B-248 | one individualized compound I | N-(Cyclopropylmethoxyimino-(6-difluoromethoxy-2,3-difluoro-phenyl)-methyl)-2-phenyl acetamide |
| B-249 | one individualized compound I | N'-(4-(4-chloro-3-trifluoromethyl-phenoxy)-2,5-dimethyl-phenyl)-N-ethyl-N-methyl formamidine |
| B-250 | one individualized compound I | N'-(4-(4-fluoro-3-trifluoromethyl-phenoxy)-2,5-dimethyl-phenyl)-N-ethyl-N-methyl formamidine |
| B-251 | one individualized compound I | N'-(2-methyl-5-trifluoromethyl-4-(3-trimethylsilanyl-propoxy)-phenyl)-N-ethyl-N-methyl formamidine |
| B-252 | one individualized compound I | N'-(5-difluoromethyl-2-methyl-4-(3-trimethylsilanyl-propoxy)-phenyl)-N-ethyl-N-methyl formamidine |
| B-253 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-254 | one individualized compound I | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-255 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoro-methyl)-1H-pyrazol-1-yl]ethanone |
| B-256 | one individualized compound I | Methoxy-acetic acid 6-tert-butyl-8-fluoro-2,3-dimethyl-quinolin-4-yl ester |
| B-257 | one individualized compound I | N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thiazolecarboxamide |
| B-258 | one individualized compound I | *Bacillus subtilis* NRRL No. B-21661 |
| B-259 | one individualized compound I | *Bacillus pumilus* NRRL No. B-30087 |
| B-260 | one individualized compound I | *Ulocladium oudemansii* |
| B-261 | one individualized compound I | Carbaryl |
| B-262 | one individualized compound I | Carbofuran |
| B-263 | one individualized compound I | Carbosulfan |

TABLE B-continued

Composition comprising one indiviualized compound I
and one further active substance from groups A) to O)

| Mixture | Component 1 | Component 2 |
|---|---|---|
| B-264 | one individualized compound I | Methomylthiodicarb |
| B-265 | one individualized compound I | Bifenthrin |
| B-266 | one individualized compound I | Cyfluthrin |
| B-267 | one individualized compound I | Cypermethrin |
| B-268 | one individualized compound I | alpha-Cypermethrin |
| B-269 | one individualized compound I | zeta-Cypermethrin |
| B-270 | one individualized compound I | Deltamethrin |
| B-271 | one individualized compound I | Esfenvalerate |
| B-272 | one individualized compound I | Lambda-cyhalothrin |
| B-273 | one individualized compound I | Permethrin |
| B-274 | one individualized compound I | Tefluthrin |
| B-275 | one individualized compound I | Diflubenzuron |
| B-276 | one individualized compound I | Flufenoxuron |
| B-277 | one individualized compound I | Lufenuron |
| B-278 | one individualized compound I | Teflubenzuron |
| B-279 | one individualized compound I | Spirotetramate |
| B-280 | one individualized compound I | Clothianidin |
| B-281 | one individualized compound I | Dinotefuran |
| B-282 | one individualized compound I | Imidacloprid |
| B-283 | one individualized compound I | Thiamethoxam |
| B-284 | one individualized compound I | Acetamiprid |
| B-285 | one individualized compound I | Thiacloprid |
| B-286 | one individualized compound I | Endosulfan |
| B-287 | one individualized compound I | Fipronil |
| B-288 | one individualized compound I | Abamectin |
| B-289 | one individualized compound I | Emamectin |
| B-290 | one individualized compound I | Spinosad |
| B-291 | one individualized compound I | Spinetoram |
| B-292 | one individualized compound I | Hydramethylnon |
| B-293 | one individualized compound I | Chlorfenapyr |
| B-294 | one individualized compound I | Fenbutatin oxide |
| B-295 | one individualized compound I | Indoxacarb |
| B-296 | one individualized compound I | Metaflumizone |
| B-297 | one individualized compound I | Flonicamid |
| B-298 | one individualized compound I | Lubendiamide |
| B-299 | one individualized compound I | Chlorantraniliprole |
| B-300 | one individualized compound I | Cyazypyr (HGW86) |
| B-301 | one individualized compound I | Cyflumetofen |
| B-302 | one individualized compound I | Acetochlor |
| B-303 | one individualized compound I | Dimethenamid |
| B-304 | one individualized compound I | metolachlor |
| B-305 | one individualized compound I | Metazachlor |
| B-306 | one individualized compound I | Glyphosate |
| B-307 | one individualized compound I | Glufosinate |
| B-308 | one individualized compound I | Sulfosate |
| B-309 | one individualized compound I | Clodinafop |
| B-310 | one individualized compound I | Fenoxaprop |
| B-311 | one individualized compound I | Fluazifop |
| B-312 | one individualized compound I | Haloxyfop |
| B-313 | one individualized compound I | Paraquat |
| B-314 | one individualized compound I | Phenmedipham |
| B-315 | one individualized compound I | Clethodim |
| B-316 | one individualized compound I | Cycloxydim |
| B-317 | one individualized compound I | Profoxydim |
| B-318 | one individualized compound I | Sethoxydim |
| B-319 | one individualized compound I | Tepraloxydim |
| B-320 | one individualized compound I | Pendimethalin |
| B-321 | one individualized compound I | Prodiamine |
| B-322 | one individualized compound I | Trifluralin |
| B-323 | one individualized compound I | Acifluorfen |
| B-324 | one individualized compound I | Bromoxynil |
| B-325 | one individualized compound I | Imazamethabenz |
| B-326 | one individualized compound I | Imazamox |
| B-327 | one individualized compound I | Imazapic |
| B-328 | one individualized compound I | Imazapyr |
| B-329 | one individualized compound I | Imazaquin |
| B-330 | one individualized compound I | Imazethapyr |
| B-331 | one individualized compound I | 2,4-Dichlorophenoxyacetic acid (2,4-D) |
| B-332 | one individualized compound I | Chloridazon |
| B-333 | one individualized compound I | Clopyralid |
| B-334 | one individualized compound I | Fluroxypyr |
| B-335 | one individualized compound I | Picloram |
| B-336 | one individualized compound I | Picolinafen |
| B-337 | one individualized compound I | Bensulfuron |
| B-338 | one individualized compound I | Chlorimuron-ethyl |

TABLE B-continued

Composition comprising one indiviualized compound I
and one further active substance from groups A) to O)

| Mixture | Component 1 | Component 2 |
|---|---|---|
| B-339 | one individualized compound I | Cyclosulfamuron |
| B-340 | one individualized compound I | Iodosulfuron |
| B-341 | one individualized compound I | Mesosulfuron |
| B-342 | one individualized compound I | Metsulfuron-methyl |
| B-343 | one individualized compound I | Nicosulfuron |
| B-344 | one individualized compound I | Rimsulfuron |
| B-345 | one individualized compound I | Triflusulfuron |
| B-346 | one individualized compound I | Atrazine |
| B-347 | one individualized compound I | Hexazinone |
| B-348 | one individualized compound I | Diuron |
| B-349 | one individualized compound I | Florasulam |
| B-350 | one individualized compound I | Pyroxasulfone |
| B-351 | one individualized compound I | Bentazone |
| B-352 | one individualized compound I | Cinidon-ethyl |
| B-353 | one individualized compound I | Cinmethylin |
| B-354 | one individualized compound I | Dicamba |
| B-355 | one individualized compound I | Diflufenzopyr |
| B-356 | one individualized compound I | Quinclorac |
| B-357 | one individualized compound I | Quinmerac |
| B-358 | one individualized compound I | Mesotrione |
| B-359 | one individualized compound I | Saflufenacil |
| B-360 | one individualized compound I | Topramezone |
| B-361 | one individualized compound I | 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-362 | one individualized compound I | 1-[rel-(2S; 3R)-3-(2-chlorophenyl)-2-(2,4-difluorophenyl)-oxiranylmethyl]-5-thiocyanato-1H-[1,2,4]triazole, |
| B-363 | one individualized compound I | 2-[rel-(2S; 3R)-3-(2-chlorophenyl)-2-(2,4-difluorophenyl)-oxiranylmethyl]-2H-[1,2,4]triazole-3-thiol |
| B-364 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone |
| B-365 | one individualized compound I | 2,6-dimethyl-1H,5H-[1,4]dithiino[2,3-c:5,6-c']dipyrrole-1,3,5,7(2H,6H)-tetraone |
| B-366 | one individualized compound I | flupyradifurone, |
| B-367 | one individualized compound I | 3-(difluoromethyl)-1-methyl-N-(1,1,3-trimethylindan-4-yl)pyrazole-4-carboxamide |
| B-368 | one individualized compound I | 3-(trifluoromethyl)-1-methyl-N-(1,1,3-trimethylindan-4-yl)pyrazole-4-carboxamide |
| B-369 | one individualized compound I | 1,3-dimethyl-N-(1,1,3-trimethylindan-4-yl)pyrazole-4-carboxamide |
| B-370 | one individualized compound I | 3-(trifluoromethyl)-1,5-dimethyl-N-(1,1,3-trimethylindan-4-yl)pyrazole-4-carboxamide |
| B-371 | one individualized compound I | 3-(difluoromethyl)-1,5-dimethyl-N-(1,1,3-trimethylindan-4-yl)pyrazole-4-carboxamide |
| B-372 | one individualized compound I | 1,3,5-trimethyl-N-(1,1,3-trimethylindan-4-yl)pyrazole-4-carboxamide |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657).

The mixtures of active substances can be prepared as compositions comprising besides the active ingredients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

With due modification of the starting compounds, the procedures shown in the synthesis examples below were used to obtain further compounds I. The resulting compounds, together with physical data, are listed in Table I below.

Example 1

Preparation of 2-[2-chloro-4-(4-chloro-phenoxy)-phenyl]-1-[1,2,4]triazol-1-yl-pentan-2-ol (Compound I-2)

MgBr diethyl etherate (10.5 g, 40.2 mmol) was added to a solution of the abovementioned ethanone (6.0 g, 16.8 mmol) in dichloromethane (DCM, 65 ml) and the mixture stirred at room temperature for about 90 min. This mixture was then cooled to about 0° C. and n-propylmagnesium chloride (22.8 ml of a 2 M solution in THF, 45.6 mmol) was added dropwise. After stirring for about two hours, the mixture was allowed to warm to room temperature and was then quenched by addition of a saturated ammonium chloride solution. The organic components were extracted three times with DCM, the organic phases combined, washed again with saturated ammonium chloride solution, dried and the solvents evaporated. Addition of diisopropyl ether resulted in precipitation of the unreacted starting material, which was filtered off. The filtrate was then purified using reverse phase chromatography, to give the product as a light brown coloured solid (2.5 g, 36%; HPLC[1] $R_t$=3.877 min)

Example 2

Preparation of 2-[2-chloro-4-(4-chloro-phenoxy)-phenyl]-1-[1,2,4]triazol-1-yl-pentan-2-ol (Compound I-2)

The intermediate 1-[2-chloro-4-(4-chloro-phenoxy)-phenyl]-2-[1,2,4]triazol-1-ylethanone was prepared as described in WO 2010/146114.

MgBr diethyl etherate (10.5 g, 40.2 mmol) was added to a solution of the above-mentioned ethanone (6.0 g, 16.8 mmol) in dichloromethane (DCM, 65 ml) and the mixture stirred at room temperature for about 90 min. This mixture was then cooled to about 0° C. and n-propylmagnesium chloride (22.8 ml of a 2 M solution in THF, 45.6 mmol) was added dropwise. After stirring for about two hours, the mixture was allowed to warm to room temperature and was then quenched by addition of a saturated ammonium chloride solution. The organic components were extracted three times with DCM, the organic phases combined, washed again with saturated ammonium chloride solution, dried and the solvents evaporated. Addition of diisopropyl ether resulted in precipitation of the unreacted starting material, which was filtered off. The filtrate was then purified using reverse phase chromatography, to give the product as a light brown colored solid (2.5 g, 36%, HPLC[2] $R_t$=1.26 min, masse=392).

Example 2

Preparation of 2-[2-chloro-4-(4-chlorophenoxy)phenyl]-1-(1,2,4-triazol-1-yl)pent-3-yn-2-ol (Compound I-8)

The intermediate 1-[2-chloro-4-(4-chloro-phenoxy)-phenyl]-2-[1,2,4]triazol-1-ylethanone was prepared as described in WO 2010/146114.

To a solution of the above-mentioned ethanone (75.5 g, 216.8 mmol) dissolved in THF (450 mL) was added a solution of $LaCl_3$.2LiCl (395.9 mL, 0.6 M in THF) at room temperature and stirred for 1 hour. The resulting solution was added dropwise to 1-propynylmagnesium bromide (650.5 mL, 0.5M in THF) at room temperature. After 1 hour at room temperature, the resulting mixture was quenched with a 10% aqueous solution of HCl and extracted with MTBE. The organic phase was washed with brine, dried and evaporated. The crude compound was stirred in a solution of MTBE/diisopropylether and filtrated to eliminate the starting material. The mother liquors were evaporated and purified on silica gel to give the title compound as a beige solid (31.1 g, HPLC-MS[2] $R_t$=1.15 min, masse=388, m.p=137° C.).

Example 3

Preparation of 2-[2-chloro-4-(4-chlorophenoxy)phenyl]-1-(1,2,4-triazol-1-yl)butan-2-ol (Compound I-1)

Step1:

To a solution of 1-bromo-2-chloro-4-(4-chlorophenoxy) benzene (410.0 g, 1.29 mol) in 1 L of THF was added dropwise isopropyl magnesium chloride (1.289 L, 1.3 M in THF) at room temperature and stirred for 30 min. The reaction mixture was then added dropwise to a solution of propanoyl chloride (155.08 g, 1.68 mol), aluminium trichloride (5.66 g, 40 mmol), lithium chloride (3.6 g, 80 mmol) and copper chloride (4.2 g, 40 mmol) in 3 L of THF under light cooling (between 20 and 30° C.). After 30 min at room temperature, the resulting mixture was quenched with an aqueous solution of ammonium chloride at 10° C. and extracted with MTBE. The organic phase was washed successively with an aqueous solution of water, then sodium chloride, dried and evaporated to give after distillation 1-[2-chloro-4-(4-chlorophenoxy)phenyl]propan-1-one (297.0 g, bp=162-168° C., P=1 mbar).

Step2

To a solution of sodium hydride (35.72 g, 1.49 mol) in THF (1 L) and dry DMSO (2 L) was added under argon drop wise at 5° C. a solution of trimethylsulfonium iodide (290.5 g, 1.42 mol) in dry DMSO (2 L). The mixture was stirred 1 hour at 5° C. followed by a dropwise addition of 1-[2-chloro-4-(4-chlorophenoxy)phenyl]propan-1-one (199.0 g, 0.65 mol) in DMSO (500 mL). The resulting mixture was then warmed to room temperature overnight and quenched with an aqueous solution of ammonium chloride and iced water, and then extracted with MTBE. The organic solvents were washed with water, dried and evaporated to give 2-[2-chloro-4-(4-chlorophenoxy)phenyl]-2-ethyl-oxirane as a yellowish solid (216.0 g, 97%). $^1$H-NMR (CDCl$_3$; 400 MHz)••(ppm)=0.9 (t, 3H); 1.75 (m, 1H); 2.10 (m, 1H); 2.80 (d, 1H); 3.05 (d, 1H); 6.85 (d, 1H); 6.95 (m, 3H); 7.30 (d, 2H); 7.40 (d, 1H).

Step 3

To 2-[2-chloro-4-(4-chlorophenoxy)phenyl]-2-ethyl-oxirane (216.0 g, 0.63 mol) dissolved in N-methyl-2-pyrrolidon (2 L) was added sodium hydroxide (62.87 g, 1.57 mol) and triazole (217.1 g, 3.14 mol) at room temperature. The mixture was then stirred for 12 hours at 140° C. A solution of ammonium chloride and ice water was then added, the mixture extracted with MTBE and washed with an aqueous solution of lithium chloride. The crude residue was purified by recrystallization in diisopropylether to give 2-[2-chloro-4-(4-chlorophenoxy)phenyl]-1-(1,2,4-triazol-1-yl)butan-2-ol compound as a colorless solid (127.0 g, 51%; m.p.=140-142° C.).

The compounds I listed in Table I have been prepared in an anlaogous manner.

TABLE I

| ex.-no. | $R^1$ | $HPLC^1$ $R_t$ (min) | $HPLC^2$ $R_t$ (min) | m.p. (° C.) |
|---|---|---|---|---|
| I-1 | —$CH_2CH_3$ | | | 140-142 |
| I-2 | —$CH_2CH_2CH_3$ | 3.877 | 1.26 | 132-135 |
| I-3 | —$CH(CH_3)_2$ | 3.545 | 1.28 | 86-87 |
| I-4 | —$CH_2CH_2CH_2CH_3$ | 4.049 | 1.32 | 108-116 |
| I-5 | —$C(CH_3)_3$ | 3.480 | 1.38 | |
| I-6 | —$C_5H_9$ (cyclopentyl) | 4.093 | 1.39 | |
| I-7 | —C≡CH | 3.398 | 1.10 | 150-151 |
| I-8 | —C≡$CCH_3$ | 3.498 | 1.15 | 139 |
| I-9 | —$C_3H_5$ (cyclopropyl) | | 1.24 | 110 |
| I-10 | —CH=$CH_2$ | | 1.16 | 119 |
| I-11 | —$CH_2$C≡CH | | 1.14 | |
| I-12 | —$CH_2$CH=$CH_2$ | | 1.21 | | m.p. = melting point.
$HPLC^1$ column: RP-18 column (Chromolith Speed ROD from Merck KgaA, Germany), 50 mm × 4.6 mm with Eluent: acetonitrile + 0.1% trifluoroacetic acid (TFA)/water + 0.1% TFA (gradient from 5:95 to 95:5 in 5 min at 40° C., flow of 1.8 ml/min)
$HPLC^2$ column: column (Kinetex XB C18 1.7 μm), 50 mm × 2.1 mm with Eluent: acetonitrile + 0.1% trifluoroacetic acid (TFA)/water; (gradient from 5:95 to 95:5 in 1.5 min at 60° C., flow of 1.8 ml/min)

II. EXAMPLES OF THE ACTION AGAINST HARMFUL FUNGI

The fungicidal action of the compounds of the formula I was demonstrated by the following experiments:

A) Greenhouse Tests

The active substances were formulated separately or together as a stock solution comprising 25 mg of active substance which was made up to 10 ml using a mixture of acetone and/or DMSO and the emulsifier Wettol EM 31 (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active substance concentration given below.

Use Example 1

Preventative Fungicidal Control of Early Blight on Tomatoes (*Alrernaria solani*)

Young seedlings of tomato plants were grown in pots. These plants were sprayed to run-off with an aqueous suspension containing the concentration of active ingredient mentioned in the table below. The next day, the treated plants were inoculated with an aqueous suspension of *Alternaria solani*. Then, the trial plants were immediately transferred to a humid chamber. After 5 days at 20 to 22° C. and a relative humidity close to 100%, the extent of fungal attack on the leaves was visually assessed as % diseased leaf area.

In this test, the plants which had been treated with 300 ppm of the active substance from examples I-5 and I-5, respectively, showed an infection of less than or equal to 15% whereas the untreated plants were 90% infected.

Use Example 2

Preventative Control of Grey Mold (*Botrytis cinerea*) on Leaves of Green Pepper Young seedlings of green pepper were grown in pots to the 2 to 3 leaf stage. These plants were sprayed to run-off with an aqueous suspension containing the concentration of active ingredient or their mixture mentioned in the table below. The next day the treated plants were inoculated with a spore suspension of *Botrytis cinerea* in a 2% aqueous biomalt solution. Then, the trial plants were immediately transferred to a dark, humid chamber. After 5 days at 22 to 24° C. and a relative humidity close to 100% the extent of fungal attack on the leaves was visually assessed as % diseased leaf area.

In this test, the plants which had been treated with 150 ppm of the active substance from examples I-1, I-2, I-3, I-7 and I-8, respectively, showed an infection of less than or equal to 15% whereas the untreated plants were 90% infected.

Use Example 3

Preventative Control of Brown Rust on Wheat Caused by *Puccinia recondita*

The first two developed leaves of pot-grown wheat seedling were sprayed to run-off with an aqueous suspension containing the concentration of active ingredient as described below. The next day the plants were inoculated with spores of *Puccinia recondita*. To ensure the success the artificial inoculation, the plants were transferred to a humid chamber without light and a relative humidity of 95 to 99% and 20 to 22° C. for 24 h. Then, the trial plants were cultivated for 6 days in a greenhouse chamber at 22-26° C. and a relative humidity between 65 and 70%. The extent of fungal attack on the leaves was visually assessed as % diseased leaf area.

In this test, the plants which had been treated with 300 ppm of the active substance from examples I-1, I-2, I-3, I-4, I-5, I-6, I-7 and I-8, respectively, showed an infection of less than or equal to 15% whereas the untreated plants were 90% infected.

Use Example 4

Preventative Control of Soy Bean Rust on Soy Beans Caused by *Phakopsora pachyrhizi*

Leaves of pot-grown soy bean seedlings were sprayed to run-off with an aqueous suspension containing the concentration of active ingredient as described below. The plants were allowed to air-dry. The next day the plants were inoculated with spores of *Phakopsora pachyrhizii*. To ensure the success of the artificial inoculation, the plants were transferred to a humid chamber with a relative humidity of about 95% and 23 to 27° C. for 24 h. Thereafter the trial plants were cultivated for 14 days in a greenhouse chamber at 23-27° C. and a relative humidity between 60 and 80%. The extent of fungal attack on the leaves was visually assessed as % diseased leaf area.

In this test, the plants which had been treated with 300 ppm of the active substance from examples I-1, I-2, I-4, I-6, I-7 and I-8, respectively, showed an infection of less than or equal to 15% whereas the untreated plants were 90% infected.

Use Example 5

Preventative Control of Leaf Blotch on Wheat Caused by *Septoria tritici*

The first two developed leaves of pot-grown wheat seedling were sprayed to run-off with an aqueous suspension containing the concentration of active ingredient as described below. The next day the plants were inoculated with a spore suspension in water of *Septoria tritici*. To ensure the success the artificial inoculation, the plants were transferred for 4 days to a humid chamber with a relative humidity of 95 to 99% and 20 to 24° C. Thereafter the plants were cultivated for 4 weeks at a relative humidity of 70%. The extent of fungal attack on the leaves was visually assessed as % diseased leaf area.

In this test, the plants which had been treated with 300 ppm of the active substance from examples I-1, I-2, I-3, I-4, I-6, I-7 and I-8, respectively, showed an infection of less than or equal to 15% whereas the untreated plants were 90% infected.

B) Microtest

The active compounds were formulated separately as a stock solution having a concentration of 10000 ppm in dimethyl sulfoxide.

Example 1

Activity Against the Late Blight Pathogen *Phytophthora infestans* in the Microtiter Test The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds.

The pathogens treated with an aqueous active compound preparation comprising 32 ppm of the active compounds I-11 and I-12 showed a growth of 12% and 10% respectively.

Example 2

Activity Against the Grey Mold *Botrytis cinerea* in the Microtiterplate Test

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds.

The pathogens treated with an aqueous active compound preparation comprising 32 ppm of the active compounds I-11 and I-12 showed a growth of 0% and 1% respectively.

Example 3

Activity Against Rice Blast *Pyricularia oryzae* in the Microtiterplate Test

The stock solutions were mixed according to the ratio, pipetted onto a micro titer plate (MTP) and diluted with water to the stated concentrations. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds.

The pathogens treated with an aqueous active compound preparation comprising 32 ppm of the active compounds I-11 and I-12 showed a growth of 0%.

Example 4

Activity Against Leaf Blotch on Wheat Caused by *Septoria tritici*

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds.

The pathogens treated with an aqueous active compound preparation comprising 32 ppm of the active compounds I-11 and I-12 showed a growth of 9% and 17% respectively.

Example 5

Activity Against Early Blight Caused by *Alternaria solani*

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds.

The pathogens treated with an aqueous active compound preparation comprising 32 ppm of the active compounds I-11 and I-12 showed a growth of 2% and 3% respectively.

Example 6

Activity Against Wheat Leaf Spots Caused by *Leptosphaeria nodorum*

The stock solutions were mixed according to the ratio, pipetted onto a micro titer plate (MTP) and diluted with water to the stated concentrations. A spore suspension of *Leptosphaeria nodorum* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. The measured parameters were compared to the growth of the active compound-free control variant (100%) and the fungus-free and active compound-free blank value to determine the relative growth in % of the pathogens in the respective active compounds.

The pathogens treated with an aqueous active compound preparation comprising 32 ppm of the active compounds I-11 and I-12 showed a growth of 2% and 4% respectively.

B) Comparative Tests

B.1 Microtest

The active compounds were formulated separately as a stock solution having a concentration of 10000 ppm in dimethyl sulfoxide.

Example 1

Activity Against Net Blotch *Pyrenophora teres* on Barley in the Microtiter Test The stock solutions were mixed according to the ratio, pipetted onto a micro titer plate (MTP) and diluted with water to the stated concentrations. A spore suspension of *Pyrenophora teres* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

| Compound no. | Structure | Growth (%) at 8 pm |
|---|---|---|
| according to prior art | 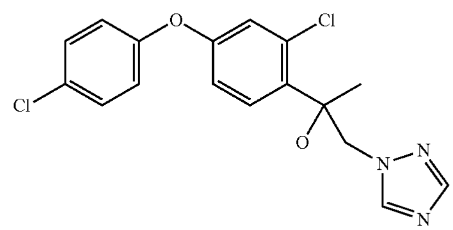 [SMILES: CC(O)(Cn1cncn1)c1ccc(Oc2ccc(Cl)cc2)cc1Cl]  | 62 |
| according to prior art | 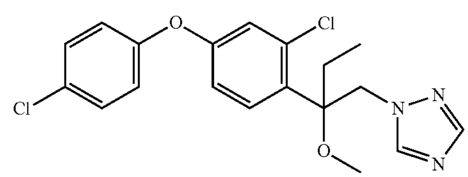 [SMILES: CCC(Cn1cncn1)(OC)c1ccc(Oc2ccc(Cl)cc2)cc1Cl]  | 39 |
| Compound Table 1, 1 according to the present invention | 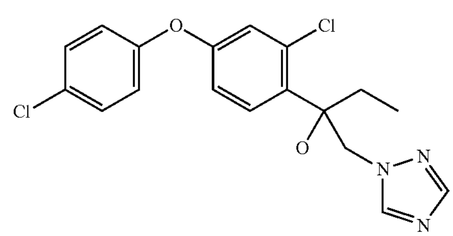 [SMILES: CCC(O)(Cn1cncn1)c1ccc(Oc2ccc(Cl)cc2)cc1Cl]  | 13 |
| according to prior art | 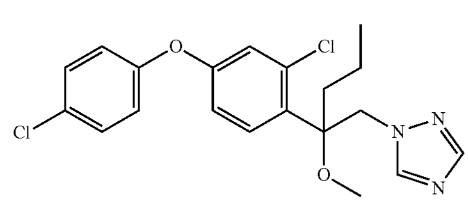 [SMILES: CCCC(Cn1cncn1)(OC)c1ccc(Oc2ccc(Cl)cc2)cc1Cl]  | 77 |

| Compound no. | Structure | Growth (%) at 8 ppm |
|---|---|---|
| Compound Table 1, 2 according to the present invention | (structure) | 57 |

Example 2

Activity Against Early Blight Caused by *Alternaria solani*

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

| Compound no. | Structure | Growth (%) at 0.5 ppm |
|---|---|---|
| according to prior art | (structure) | 91 |
| Compound Table 1, 10 according to the present invention | (structure) | 0 |

Example 3

Activity Against the Grey Mold *Botytis cinerea* in the Microtiterplate Test The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

| Compound no. | Structure | Growth (%) at 0.5 ppm |
|---|---|---|
| according to prior art | (structure) | 77 |

| Compound no. | Structure | Growth (%) at 0.5 pm |
|---|---|---|
| Compound Table 1, 10 according to the present invention | (structure) | 0 |

Example 4
Activity Against Rice Blast *Pyricularia oryzae* in the Microtiterplate Test The stock solutions were mixed according to the ratio, pipetted onto a micro titer plate (MTP) and diluted with water to the stated concentrations. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies.

| Compound no. | Structure | Growth (%) at 0.5 pm |
|---|---|---|
| according to prior art | (structure) | 30 |
| Compound Table 1, 2 according to the present invention | (structure) | 4 |

Example 5
Activity Against Early Blight Caused by *Alternaria solani*

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

| Compound no. | Structure | Growth (%) at 0.000125 pm |
|---|---|---|
| according to prior art | (structure) | 45 |

| Compound no. | Structure | Growth (%) at 0.000125 pm |
|---|---|---|
| according to prior art | 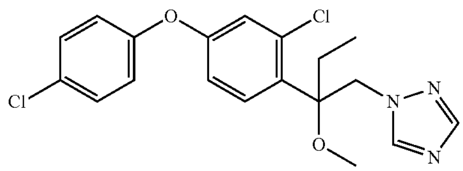 [SMILES: CCC(Cn1cncn1)(OC)c1ccc(Oc2ccc(Cl)cc2)cc1Cl] | 83 |
| Compound Table 1, 1 according to the present invention | 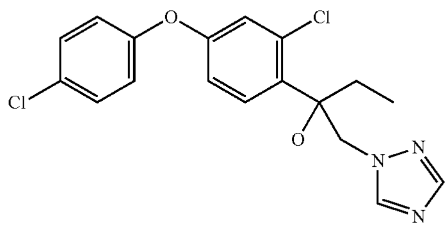 [SMILES: CCC(O)(Cn1cncn1)c1ccc(Oc2ccc(Cl)cc2)cc1Cl] | 1 |
| Compound Table 1, 32 according to the present invention | 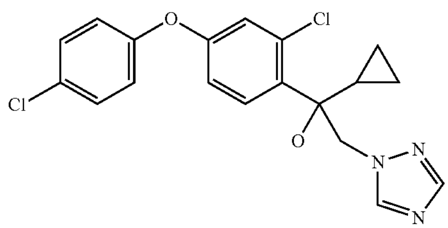 [SMILES: OC(Cn1cncn1)(c1ccc(Oc2ccc(Cl)cc2)cc1Cl)C1CC1] | 1 |

Example 7

Activity Against Rice Blast *Pyricularia oryzae* in the Microtiterplate Test The stock solutions were mixed according to the ratio, pipetted onto a micro titer plate (MTP) and diluted with water to the stated concentrations. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

| Compound no. | Structure | Growth (%) at 0.5 pm |
|---|---|---|
| according to prior art | | 82 |
| according to prior art | | 47 |
| Compound Table 1, 1 according to the present invention | 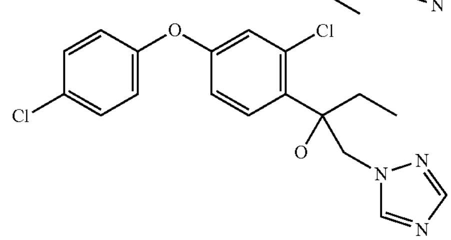 | 15 |

B.2 Green House

The spray solutions were prepared in several steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml.

Water was then added to total volume of 100 ml.

This stock solution was diluted with the described solvent-emulsifier-water mixture to the given concentration.

Example 1
Preventative Control of Leaf Blotch on Wheat Caused by *Septonia tritici*

Leaves of pot-grown wheat seedling were sprayed to run-off with an aqueous suspension of the active compound or their mixture, prepared as described. The plants were allowed to air-dry. At the following day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

| Compound no. | Structure | Disease (%) at 150 ppm |
|---|---|---|
| according to prior art | | 60 |
| according to prior art | | 50 |
| Compound Table 1, 1 according to the present invention | 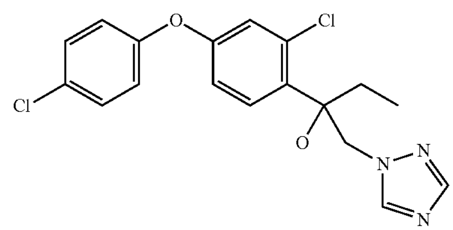 [SMILES: CCC(O)(Cn1cncn1)c1ccc(Oc2ccc(Cl)cc2)cc1Cl] | 10 |
| Untreated control | | 90 |

Example 2
Fungicidal Control of Rice Blast Caused by *Pyricularia oryzae*

Leaves of pot-grown rice seedlings were sprayed to run-off with an aqueous suspension of the compound prepared as described. Seven days later the plants were inoculated with an aqueous spore suspension of *Pyricularia oryzae*. Then the trial plants were immediately transferred to a humid chamber. After 6 days at 22-24° C. and a relative humidity close to 100% the extent of fungal attack on the leaves was visually assessed as % diseased leaf area.

| Compound no. | Structure | Disease (%) at 250 ppm |
|---|---|---|
| according to prior art | 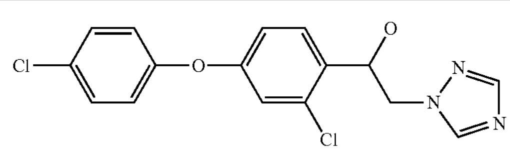 [SMILES: OC(Cn1cncn1)c1ccc(Oc2ccc(Cl)cc2)cc1Cl] | 60 |

| Compound no. | Structure | Disease (%) at 250 ppm |
|---|---|---|
| Compound Table 1, 1 according to the present invention | (structure) | 20 |
| Untreated control | | 90 |

Example 3

Control of Culm Rot on Pearl Millet Caused by *Fusarium culmorum*

Pot-grown pearl millet seedlings with 2-3 leaves were sprayed to run-off with an aqueous suspension of the compound prepared as described. The plants were allowed to air-dry. At the following day the plants were inoculated with an spore suspension of *Fusarium culmorum* in a 2% aqueous malt solution. Then the trial plants were immediately transferred to a humid chamber. After 6 days at 23-25° C. and a relative humidity close to 100% the extent of fungal attack on the leaves was visually assessed as % diseased leaf area.

| Compound no. | Structure | Disease (%) at 16 ppm |
|---|---|---|
| according to prior art | (structure) | 25 |
| Compound Table 1, 1 according to the present invention | (structure) | 1 |
| Compound Table 1, 32 according to the present invention | (structure) | 5 |
| according to prior art | (structure) | 30 |

| Compound no. | Structure | Disease (%) at 16 ppm |
|---|---|---|
| Compound Table 1, 1 according to the present invention | 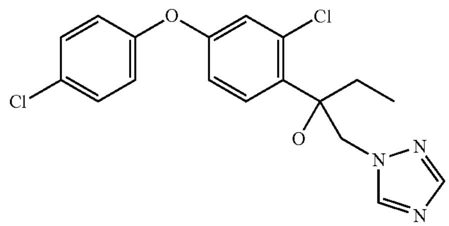 [SMILES: CCC(O)(Cn1cncn1)c1ccc(Oc2ccc(Cl)cc2)cc1Cl] | 0 |
| Untreated control | | 90 |

Example 4
Curative Control of Leaf Blotch on Wheat Caused by *Septoria tritici*

Leaves of pot-grown wheat seedling were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. Seven days after inoculation the plants were sprayed to run-off with an aqueous suspension of the active compound or their mixture, prepared as described. Then the plants were transferred back to the chamber with 18-22° C. and a relative humidity close to 70%. After 4 weeks the extent of fungal attack on the leaves was visually assessed as % diseased leaf area.

| Compound no. | Structure | Disease (%) at 16 ppm |
|---|---|---|
| according to prior art | 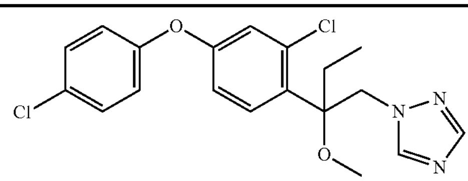 | 70 |
| Compound Table 1, 1 according to the present invention | 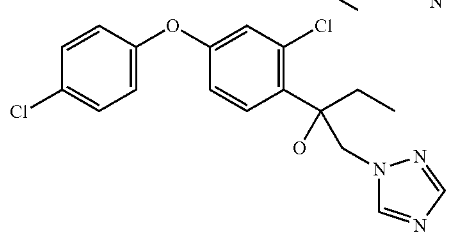 | 40 |
| Untreated control | | 90 |

The invention claimed is:
1. A compound of formula I

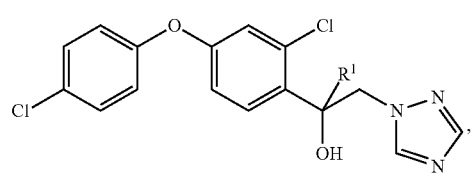

wherein:
R¹ is selected from the group consisting of $C_2$-$C_6$-alkyl, $C_2$-$C_6$-alkenyl, $C_2$-$C_6$-alkynyl, $C_3$-$C_8$-cycloalkyl and $C_3$-$C_8$-cycloalkyl-$C_1$-$C_4$-alkyl;
wherein the aliphatic groups R¹ are unsubstituted or carry 1, 2, 3 or 4 CN substituents;
wherein the cycloalkyl moieties of R¹ are unsubstituted or carry 1, 2, 3 or up to the maximum number of identical or different groups $R^b$ which independently of one another are selected from:
$R^b$ is selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy;
or an N-oxide or an agriculturally acceptable salt thereof, except for 2-[2-chloro-4-(4-chloro-phenoxy)-phenyl]-1-[1,2,4]triazol-1-yl-pent-4-yn-2-ol.

2. The compound of claim 1, wherein R¹ is $C_2$-$C_6$-alkyl, $C_2$-$C_6$-alkenyl or $C_2$-$C_6$-alk-1-ynyl.

3. The compound of claim 2, wherein R¹ is $C_2$-$C_4$-alkyl.

4. The compound of claim 1, wherein R¹ is $C_2$-$C_6$-alkenyl or $C_2$-$C_6$-alk-1-ynyl.

5. The compound of claim 1, wherein R¹ is $C_3$-$C_8$-cycloalkyl or $C_3$-$C_8$-cycloalkyl-$C_1$-$C_4$-alkyl.

6. The compound of claim 1, wherein R¹ is selected from the group consisting of ethyl, n-propyl, isopropyl, n-butyl, tert.-butyl, allyl, ethynyl, prop-1-ynyl; but-1-ynyl, cyclopropyl and cyclopropylmethyl.

7. An agrochemical composition wherein said composition comprises an auxiliary and at least one compound of formula I, as defined in claim 1, an N-oxide or an agriculturally acceptable salt thereof.

8. The composition of claim 7, comprising an additional active compound.

9. A method for combating phytopathogenic fungi comprising treating the fungi or the materials, plants, the soil or seeds to be protected against fungal attack with an effective amount of a composition comprising a compound of the formula I

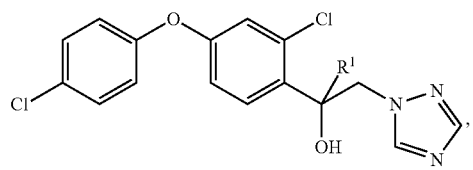

wherein:
$R^1$ is selected from the group consisting of $C_2$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl;
wherein the aliphatic groups $R^1$ are unsubstituted or carry 1, 2, 3 or 4 CN substituents;
wherein the cycloalkyl moieties of $R^1$ are unsubstituted or carry 1, 2, 3 or up to the maximum number of identical or different groups $R^b$ which independently of one another are selected from:
$R^b$ is selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy;
or an N-oxide or an agriculturally acceptable salt thereof.

10. The method of claim 9, wherein $R^1$ is $C_2$-$C_6$-alkyl, $C_2$-$C_6$-alkenyl or $C_2$-$C_6$-alk-1-ynyl.

11. The method of claim 10, wherein $R^1$ is $C_2$-$C_4$-alkyl.

12. The method of claim 9, wherein $R^1$ is $C_2$-$C_6$-alkenyl or $C_2$-$C_6$-alk-1-ynyl.

13. The method of claim 9, wherein $R^1$ is $C_3$-$C_8$-cycloalkyl or $C_3$-$C_8$-cycloalkyl-$C_1$-$C_4$-alkyl.

14. The method of claim 9, wherein $R^1$ is selected from the group consisting of ethyl, n-propyl, isopropyl, n-butyl, tert-butyl, allyl, ethynyl, prop-1-ynyl; but-1-ynyl, cyclopropyl and cyclopropylmethyl.

15. A method for protecting plant propagation material and seedlings' roots and shoots from infestation by harmful fungi comprising contacting the plant propagation material with a composition comprising a compound of claim 1.

16. A seed coated with at least one compound of formula I as defined in claim 1, in an amount of from 0.1 g to 10 kg per 100 kg of seed.

17. A process for preparing the compound of claim 1, comprising reacting a compound of formula III

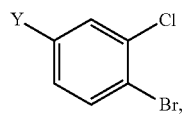

wherein Y is F or Cl,
with 4-chlorophenol of formula II

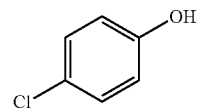

under basic conditions;
and reacting the resulting compound of formula IV

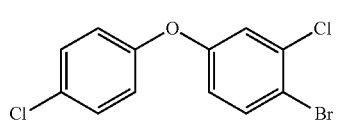

in the presence of a catalyst with isopropylmagnesium bromide followed by a reaction with acetyl chloride;
halogenating the resulting compound of formula V

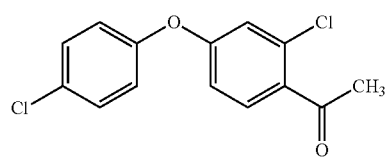

with bromine;
reacting the resulting compound of formula VI

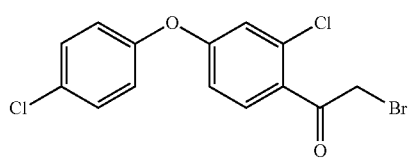

under basic conditions with 1H-1,2,4-triazole;
and reacting the resulting compound of formula VII

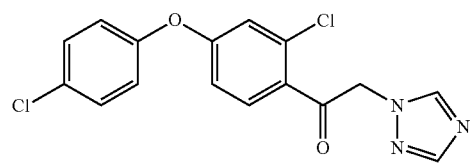

with a compound of formula VIII $R^1$-M,
wherein $R^1$ is selected from the group consisting of $C_2$-$C_6$-alkyl, $C_2$-$C_6$-alkenyl, $C_2$-$C_6$-alkynyl, $C_3$-$C_8$-cycloalkyl and $C_3$-$C_8$-cycloalkyl-$C_1$-$C_4$-alkyl;
wherein the aliphatic groups $R^1$ are unsubstituted or carry 1, 2, 3 or 4 CN substituents;
wherein the cycloalkyl moieties of $R^1$ are unsubstituted or carry 1, 2, 3 or up to the maximum number of identical or different groups $R^b$ which independently of one another are selected from:
$R^b$ is selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy and M is selected from the group consisting of MgBr, MgCl, Li and Na, to obtain compounds I.

18. A process for preparing the compound of claim 1, comprising reacting a compound of formula III

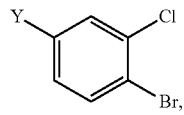

III wherein Y is F or Cl,
in presence of a catalyst with isopropylmagnesium halide followed by a reaction with a compound of formula IX
$R^1$—COCl,
wherein $R^1$ is selected from the group consisting of $C_2$-$C_6$-alkyl, $C_2$-$C_6$-alkenyl, $C_2$-$C_6$-alkynyl, $C_3$-$C_8$-cycloalkyl or $C_3$-$C_8$-cycloalkyl-$C_1$-$C_4$-alkyl;
wherein the aliphatic groups $R^1$ are unsubstituted or carry 1, 2, 3 or 4 CN substituents;
wherein the cycloalkyl moieties of $R^1$ are unsubstituted or carry 1, 2, 3 or up to the maximum number of identical or different groups $R^b$ which independently of one another are selected from:
$R^b$ is selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy;
and the N-oxides and the agriculturally acceptable salts thereof,
converting the resulting compound of formula X

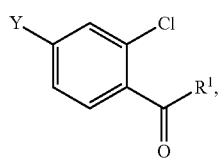

X wherein Y is F or Cl;
under basic conditions with 4-chlorophenole of formula II

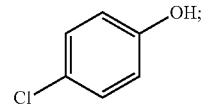

II and reacting the resulting compound of formula Va

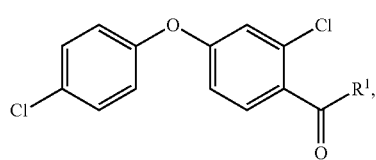

Va with trimethylsulf(ox)onium halide;
and reacting the resulting compound of formula XI

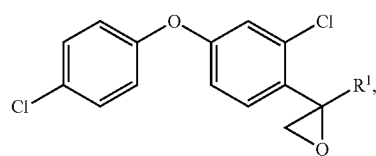

XI under basic conditions with 1H-1,2,4-triazole, to obtain compounds of formula I.

* * * * *